(12) United States Patent
Yajima

(10) Patent No.: US 10,973,400 B2
(45) Date of Patent: Apr. 13, 2021

(54) OPTICAL FIBER SCANNER AND SCANNING ENDOSCOPE APPARATUS

(71) Applicant: OLYMPUS CORPORATION, Tokyo (JP)

(72) Inventor: Hiroyoshi Yajima, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 820 days.

(21) Appl. No.: 15/666,936

(22) Filed: Aug. 2, 2017

(65) Prior Publication Data

US 2017/0354323 A1   Dec. 14, 2017

Related U.S. Application Data

(63) Continuation of application No. PCT/JP2015/000562, filed on Feb. 6, 2015.

(51) Int. Cl.
| | | |
|---|---|---|
| A61B 1/07 | (2006.01) | |
| A61B 1/06 | (2006.01) | |
| G02B 6/12 | (2006.01) | |
| A61B 1/00 | (2006.01) | |
| A61B 1/04 | (2006.01) | |

(52) U.S. Cl.
CPC ............ *A61B 1/07* (2013.01); *A61B 1/00006* (2013.01); *A61B 1/00009* (2013.01); *A61B 1/00096* (2013.01); *A61B 1/00105* (2013.01); *A61B 1/00126* (2013.01); *A61B 1/00165* (2013.01); *A61B 1/00188* (2013.01); *A61B 1/042* (2013.01); *A61B 1/0638* (2013.01); *A61B 1/0669* (2013.01); *A61B 1/00172* (2013.01)

(58) Field of Classification Search
CPC .... A61B 1/07; A61B 1/00006; A61B 1/00009
USPC .......................................................... 385/115
See application file for complete search history.

(56) References Cited

U.S. PATENT DOCUMENTS

| | | | | |
|---|---|---|---|---|
| 5,115,814 A | * | 5/1992 | Griffith .................... | A61B 5/06 600/439 |
| 5,176,140 A | * | 1/1993 | Kami ....................... | A61B 8/12 310/327 |
| 5,682,412 A | * | 10/1997 | Skillicorn ................ | A61B 6/06 378/113 |

(Continued)

FOREIGN PATENT DOCUMENTS

| | | |
|---|---|---|
| JP | 2008-521022 A | 6/2008 |
| JP | 2008-165236 A | 7/2008 |

(Continued)

OTHER PUBLICATIONS

Japanese Office Action dated Aug. 21, 2018 in Japanese Patent Application No. 2016-572941.

(Continued)

*Primary Examiner* — Kaveh C Kianni
(74) *Attorney, Agent, or Firm* — Scully, Scott, Murphy & Presser, P.C.

(57) ABSTRACT

Provided is an optical fiber scanner capable of generating an image with excellent image quality, which displaces an emission end of an optical fiber by means of an optical scanning actuator and scans light emitted from the optical fiber, in which the optical fiber 31 includes a photonic crystal fiber at least in a propagation path of the light leading to the optical scanning actuator.

2 Claims, 8 Drawing Sheets

(56) References Cited

U.S. PATENT DOCUMENTS

| | | | | |
|---|---|---|---|---|
| 5,838,000 | A * | 11/1998 | Mertesdorf | B82Y 20/00 250/234 |
| 6,687,010 | B1 * | 2/2004 | Horii | G01B 9/0201 356/479 |
| 6,845,190 | B1 * | 1/2005 | Smithwick | A61B 1/0008 385/1 |
| 7,129,472 | B1 * | 10/2006 | Okawa | A61B 1/00059 250/234 |
| 2001/0007917 | A1 * | 7/2001 | Hayakawa | B29C 48/34 600/139 |
| 2003/0020922 | A1 * | 1/2003 | Crowley | G01B 9/02028 356/502 |
| 2004/0151466 | A1 * | 8/2004 | Crossman-Bosworth | G02B 6/25 385/140 |
| 2004/0156124 | A1 * | 8/2004 | Okada | G02B 27/021 359/754 |
| 2004/0158129 | A1 * | 8/2004 | Okada | A61B 1/05 600/168 |
| 2004/0181148 | A1 * | 9/2004 | Uchiyama | G01N 21/474 600/425 |
| 2004/0254474 | A1 * | 12/2004 | Seibel | A61B 5/0066 600/473 |
| 2006/0013528 | A1 * | 1/2006 | Rosman | G02B 26/101 385/25 |
| 2006/0132791 | A1 * | 6/2006 | Toida | A61B 5/0066 356/479 |
| 2006/0170930 | A1 * | 8/2006 | Li | G01B 9/02091 356/479 |
| 2006/0241493 | A1 * | 10/2006 | Feldman | A61B 8/4461 600/476 |
| 2006/0244973 | A1 * | 11/2006 | Yun | G01B 9/02091 356/511 |
| 2006/0255250 | A1 * | 11/2006 | Chong | G02B 26/0858 250/227.11 |
| 2007/0016062 | A1 * | 1/2007 | Park | A61B 8/12 600/459 |
| 2007/0019906 | A1 * | 1/2007 | Melville | G02B 6/262 385/25 |
| 2007/0078305 | A1 * | 4/2007 | Teramura | G02B 23/2469 600/139 |
| 2007/0232902 | A1 * | 10/2007 | Teramura | A61B 5/6852 600/425 |
| 2007/0239032 | A1 * | 10/2007 | Milner | A61B 5/6852 600/476 |
| 2007/0244357 | A1 * | 10/2007 | Wiklof | A61B 1/00165 600/109 |
| 2007/0244365 | A1 * | 10/2007 | Wiklof | A61B 1/00096 600/173 |
| 2007/0287920 | A1 * | 12/2007 | Sawada | A61B 8/4488 600/463 |
| 2008/0004491 | A1 * | 1/2008 | Karasawa | G02B 6/241 600/101 |
| 2008/0039693 | A1 * | 2/2008 | Karasawa | A61B 1/00165 600/175 |
| 2008/0058629 | A1 * | 3/2008 | Seibel | A61B 1/00172 600/368 |
| 2008/0073517 | A1 * | 3/2008 | Melville | G02B 7/008 250/306 |
| 2008/0078939 | A1 * | 4/2008 | Hennessy | G03B 42/04 250/370.09 |
| 2008/0161648 | A1 * | 7/2008 | Karasawa | A61B 1/0017 600/182 |
| 2008/0165360 | A1 * | 7/2008 | Johnston | G06T 7/80 356/394 |
| 2008/0221388 | A1 * | 9/2008 | Seibel | A61B 1/00177 600/109 |
| 2008/0243031 | A1 * | 10/2008 | Seibel | A61B 10/02 600/566 |
| 2008/0249369 | A1 * | 10/2008 | Seibel | G02B 23/26 600/182 |
| 2009/0024191 | A1 * | 1/2009 | Seibel | A61B 1/00172 607/92 |
| 2009/0026888 | A1 * | 1/2009 | Melville | A61B 1/00172 310/335 |
| 2009/0028407 | A1 * | 1/2009 | Seibel | A61B 1/0008 382/131 |
| 2009/0208143 | A1 * | 8/2009 | Yoon | A61B 5/065 382/321 |
| 2009/0244260 | A1 * | 10/2009 | Takahashi | A61B 5/1076 348/45 |
| 2009/0316116 | A1 * | 12/2009 | Melville | A61B 1/07 353/31 |
| 2011/0235049 | A1 * | 9/2011 | Burnett | G01J 9/04 356/484 |
| 2013/0345508 | A1 * | 12/2013 | Akui | A61B 1/00172 600/109 |
| 2014/0073950 | A1 * | 3/2014 | Akui | A61B 1/07 600/478 |
| 2014/0194691 | A1 * | 7/2014 | Imaizumi | A61B 1/07 600/178 |
| 2014/0236022 | A1 * | 8/2014 | Zeng | A61B 1/0125 600/476 |
| 2014/0286604 | A1 * | 9/2014 | Gweon | G02B 26/103 385/13 |
| 2014/0323878 | A1 * | 10/2014 | Toriumi | G02B 21/0076 600/478 |
| 2015/0005579 | A1 * | 1/2015 | Yamabe | A61B 1/00057 600/109 |
| 2015/0029570 | A1 * | 1/2015 | Ito | G02B 23/24 359/198.1 |
| 2015/0080718 | A1 * | 3/2015 | Wheatley | A61B 1/00071 600/429 |
| 2015/0173603 | A1 * | 6/2015 | Wheatley | G01B 9/0205 600/425 |
| 2015/0173604 | A1 * | 6/2015 | Wheatley | G02B 26/103 600/425 |
| 2015/0320307 | A1 * | 11/2015 | Wheatley | A61B 3/102 351/206 |
| 2015/0327760 | A1 * | 11/2015 | Wheatley | A61B 3/102 351/206 |
| 2017/0176742 | A1 * | 6/2017 | Kasai | G02B 23/26 |
| 2017/0238792 | A1 * | 8/2017 | Yokota | A61B 1/07 |
| 2017/0248784 | A1 * | 8/2017 | Fujiwara | G02B 26/103 |
| 2020/0025665 | A1 * | 1/2020 | Trainer | G01N 15/0205 |

FOREIGN PATENT DOCUMENTS

| | | |
|---|---|---|
| JP | 2011-050667 A | 3/2011 |
| JP | 2015-019816 A | 2/2015 |
| WO | WO 2011/108087 A1 | 9/2011 |

OTHER PUBLICATIONS

International Search Report dated Apr. 21, 2015 issued in PCT/JP2015/000562.

International Preliminary Report on Patentability dated Aug. 17, 2017 received in PCT/JP2015/000562.

* cited by examiner

OPTICAL FIBER SCANNER AND SCANNING ENDOSCOPE APPARATUS

CROSS-REFERENCE TO RELATED APPLICATION

The present application is a Continuing Application based on International Application PCT/JP2015/000562 filed on Feb. 6, 2015, the entire disclosure of which is incorporated herein by reference.

TECHNICAL FIELD

The present disclosure relates to an optical fiber scanner and a scanning endoscope apparatus including the optical fiber scanner.

BACKGROUND

Some scanning endoscope apparatuses are known to scan an inspection site by irradiating illumination light toward the inspection site from an optical fiber extending through inside a scope while displacing, by an optical scanning actuator, the emission end of the optical fiber, and to detect light reflected from the inspection site, to thereby observe the image (see, for example, PTL 1).

CITATION LIST

Patent Literature

PTL 1: JP2008-165236A

SUMMARY

The disclosed optical fiber, having an optical scanning actuator to displace an emission end of an optical fiber and scanning light emitted from the optical fiber,
in which the optical fiber includes a photonic crystal fiber at least in a propagation path of the light leading to the optical scanning actuator.

The optical fiber may be formed entirely of the photonic crystal fiber.

The optical fiber may include a single mode fiber fused to an incident end face of the photonic crystal fiber.

The optical fiber may include a single mode fiber fused to an emission end face of the photonic crystal fiber, and the emission end of the single mode fiber may be displaced by the optical scanning actuator.

The single mode fiber fused to the emission end face of the photonic crystal fiber may be smaller in outer diameter than the photonic crystal fiber.

The optical fiber may include a gradient index lens fused to the incident end face of the fiber.

The gradient index lens and the optical fiber fused with the gradient index lens may be substantially equal to each other in outer diameter.

Further, the disclosed scanning endoscope apparatus includes:
 a casing having a light source section; and
 the aforementioned optical fiber scanner,
 in which:
 the light source section includes: a plurality of lasers that emit laser lights of different wavelengths; a coupler that multiplexes laser lights from the plurality of lasers; and a fiber that propagates light emitted from the coupler; and
 the optical fiber scanner is installed in a scope detachably connected to the casing such that, when the scope is connected to the casing, the optical fiber has an incident end face optically coupled to an emission end face of the fiber that propagates light emitted from the coupler.

Further, the disclosed scanning endoscope apparatus includes:
 a casing having a light source section; and
 an optical fiber scanner that includes a single mode fiber fused to the emission end face of the aforementioned photonic crystal fiber,
 in which:
 the light source section includes: a plurality of lasers that emit laser lights of different wavelengths; a coupler that multiplexes laser lights from the plurality of lasers; and a fiber that propagates light emitted from the coupler; and
 the optical fiber scanner is installed in a scope detachably connected to the casing such that the entire single mode fiber including a part where the single mode fiber is fused to an emission end face of the photonic crystal fiber is positioned inside a hard part of the tip part of the scope, the optical scanning actuator displaces an emission end of the single mode fiber, and an incident end face of the optical fiber is optically coupled to the emission end face of the fiber propagating light emitted from the coupler when the scope is connected to the casing.

Further, the disclosed scanning endoscope apparatus, includes:
 a casing having a light source section; and
 the aforementioned optical fiber scanner that has the gradient index lens,
 in which:
 the light source section includes: a plurality of lasers that emit laser lights of different wavelengths; a coupler that multiplexes laser lights from the plurality of lasers; a fiber that propagates light emitted from the coupler; and a gradient index lens fused to an emission end face of the fiber; and
 the optical fiber scanner is installed in a scope detachably connected to the casing, and when the scope is connected to the casing, the gradient index lens fused to an incident end face of the optical fiber is optically coupled to the gradient index lens fused to the emission end face of the fiber propagating light emitted from the coupler.

The gradient index lens of the light source section, the fiber fused with the gradient index lens, the gradient index lens of the fiber scanner, and the optical fiber fused with the gradient index lens may be substantially equal to one another in outer diameter.

The optical fiber scanner may further include a detection fiber that propagates signal light from an irradiation object irradiated with light from the optical fiber.

The detection fiber may be formed of a plurality of multimode fibers,

The light source section may further include a plurality of fibers that each propagate laser lights from the plurality of lasers; and the coupler may multiplex the laser lights from the plurality of fibers.

BRIEF DESCRIPTION OF THE DRAWINGS

In the accompanying drawings.

DETAILED DESCRIPTION

When a scanning endoscope, having a single mode fiber as an optical fiber, is applied with a strong bending (curvature radius and bending angle) within a body cavity, for example, the illumination light leaks out from the bent part, causing illumination light loss. As a result, when the optical fiber is formed of a single mode fiber in particular, illumination light with a long wavelength suffers a larger bent loss, causing changes in color balance or reduction in absolute brightness, which could lead to reduced image quality of the observed image. Such phenomena involved in scanning endoscope apparatuses similarly occurs, for example, in projectors which scan light from an optical fiber to project an image.

It could therefore be helpful to provide an optical fiber scanner and a scanning endoscope apparatus capable of generating an image of excellent image quality.

Hereinafter, Embodiments of the present disclosure will be illustrated with reference to the accompanying drawings.

Embodiment 1

Figure 1:
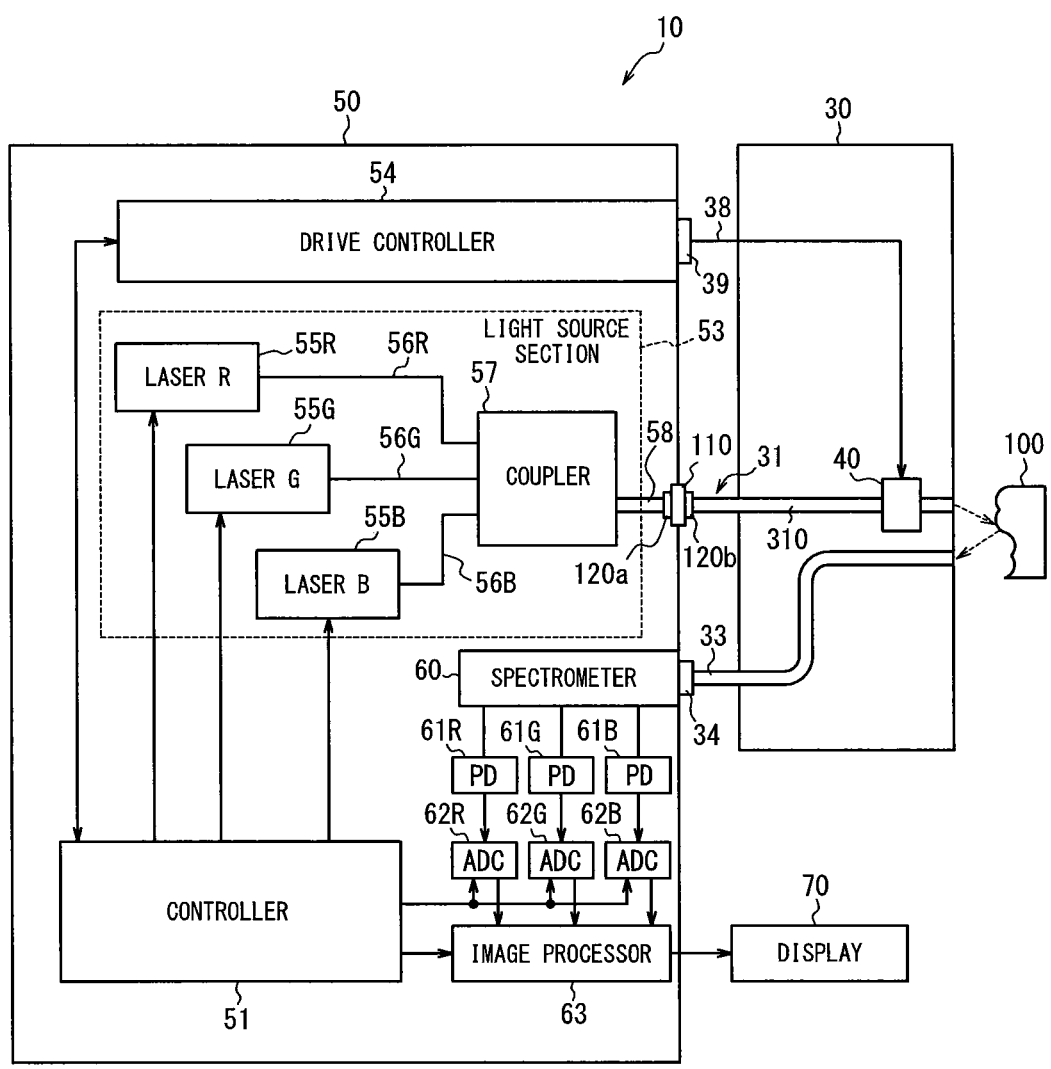
FIG. 1 is a block diagram illustrating a schematic configuration of a main part of the disclosed scanning endoscope apparatus according to Embodiment 1.

FIG. 1 is a block diagram illustrating a schematic configuration of a main part of the disclosed scanning endoscope apparatus according to Embodiment 1. The scanning endoscope apparatus 10 of Embodiment 1 includes: a scope (endoscope) 30; a control apparatus body (casing) 50; and a display 70. The control apparatus body 50 is configured by including: a controller 51 controlling the entire scanning endoscope apparatus 10; a light source section 53; and a drive controller 54.

The light source section 53 has lasers 55R, 55G, 55B, first fibers 56R, 56G, 56B, a coupler 57, and a second fiber 58. The lasers 55R, 55G, 55B are controlled by the controller 51 so that the lasers 55R, 55G, 55B each emit red laser light, green laser light, and blue laser light, respectively. A diode pumped solid state (DPSS) laser and a laser diode, for example, may be available as the lasers 55R, 55G, 55B. Here, each light has a wavelength of, for example, 440 nm to 460 nm for blue light, 515 nm to 532 nm for green light, and 635 nm to 638 nm for red light. Laser lights emitted from the lasers 55R, 55G, 55B are incident on the coupler 57 via the corresponding one of the first fibers 56R, 56G, 56B, and then caused to incident on an illumination optical fiber 31 via the second fiber 58.

The first fibers 56R, 56G, 56B are each formed of, for example, a single mode fiber, and the second fiber 58 is formed of, for example, a wide band single mode fiber. Here, the wide band single mode fiber has a core diameter of, for example, 3.5 µm and NA of 0.12. The coupler 57 is configured by including, for example, a dichroic prism. Here, an optical connector 120a may be joined to the emission end of the second fiber 58. The optical connector 120a is detachably connected to an adapter 110 fixed to the control apparatus body 50. Without being limited to the above configuration, the light source section 53 may use other plurality of light sources. Further, the light source section 53 may be accommodated in a separate casing different from the control apparatus body 50, the casing being connected via a signal line to the control apparatus body 50.

The scope 30 is detachably connected to the control apparatus body 50. When the light source section 53 is stored in a different casing from the control apparatus body 50, the illumination optical fiber 31 is detachably connected to the casing having the light source section 53. The illumination optical fiber 31 extends up to the tip part of the scope 30. An optical connector 120b, for example, may be joined to the incident end of the illumination optical fiber 31. The optical connector 120b is detachably connected to the adapter 110, and optically coupled to the optical connector 120a of the light source section 53 via the adapter 110. With this configuration, illumination light from the light source section 53 is caused to incident on the illumination optical fiber 31.

The emission end of the illumination optical fiber 31 is oscillatably supported by an optical scanning actuator 40 to be described later. Illumination light incident on the illumination optical fiber 31 is guided up to the tip part of the scope 30 and irradiated toward an object (irradiation object) 100. During the irradiation, the drive controller 54 supplies a predetermined drive signal to the optical scanning actuator 40, to thereby vibratorily drive the emission end of the illumination optical fiber 31. As a result, the object 100 is two-dimensionally scanned with illumination light emitted from the illumination optical fiber 31. Further, signal light such as reflected light, scattered light, fluorescence obtained from the object 100 irradiated with illumination light are incident on the tip end face of a detection fiber bundle 33 formed of a multimode fiber extending through inside the scope 30, and guided therethrough to the control apparatus body 50. An optical connector 34 may be joined to the emission end of the detection fiber bundle 33.

The control apparatus body 50 further includes a spectrometer 60, photodetectors (PDs) 61R, 61G, 61B, analog-digital converters (ADCs) 62R, 62G, 62B, and an image processor 63. The detection fiber bundle 33 is detachably joined to the spectrometer 60 via the optical connector 34, and guides signal light from the object 100 to the spectrometer 60. The spectrometer 60 splits signal light guided through the detection fiber bundle 33, into each color of R, G, B, and causes each color of light to incident into the corresponding one of the photodetectors 61R, 61G, 61B. The photodetectors 61R, 61G, 61B each receive incident signal light and convert the signal light thus received into an electric signal corresponding to the color of the illumination light. The ADCs 62R, 62G, 62B each convert analog electric signals output from the corresponding one of the photodetectors 61R, 61G, 61B, into digital signals, and output the digital signals to the image processor 63.

The controller 51 calculates information on the scanning position on the scanning locus of laser illumination light, based on information such as the amplitude and phase of the drive signal supplied from the drive controller 54 to the optical scanning actuator 40, and supplies the information thus calculated to the image processor 63. The image processor 63 sequentially stores pixel data (pixel values) of the object 100 based on digital signals output from the ADCs 62R, 62G, 62B and the scanning position information from the controller 51, performs necessary processing such as interpolation processing thereon after the scan or during the scan to generate an image of the object 100, and displays the image on the display 70.

Figure 2:
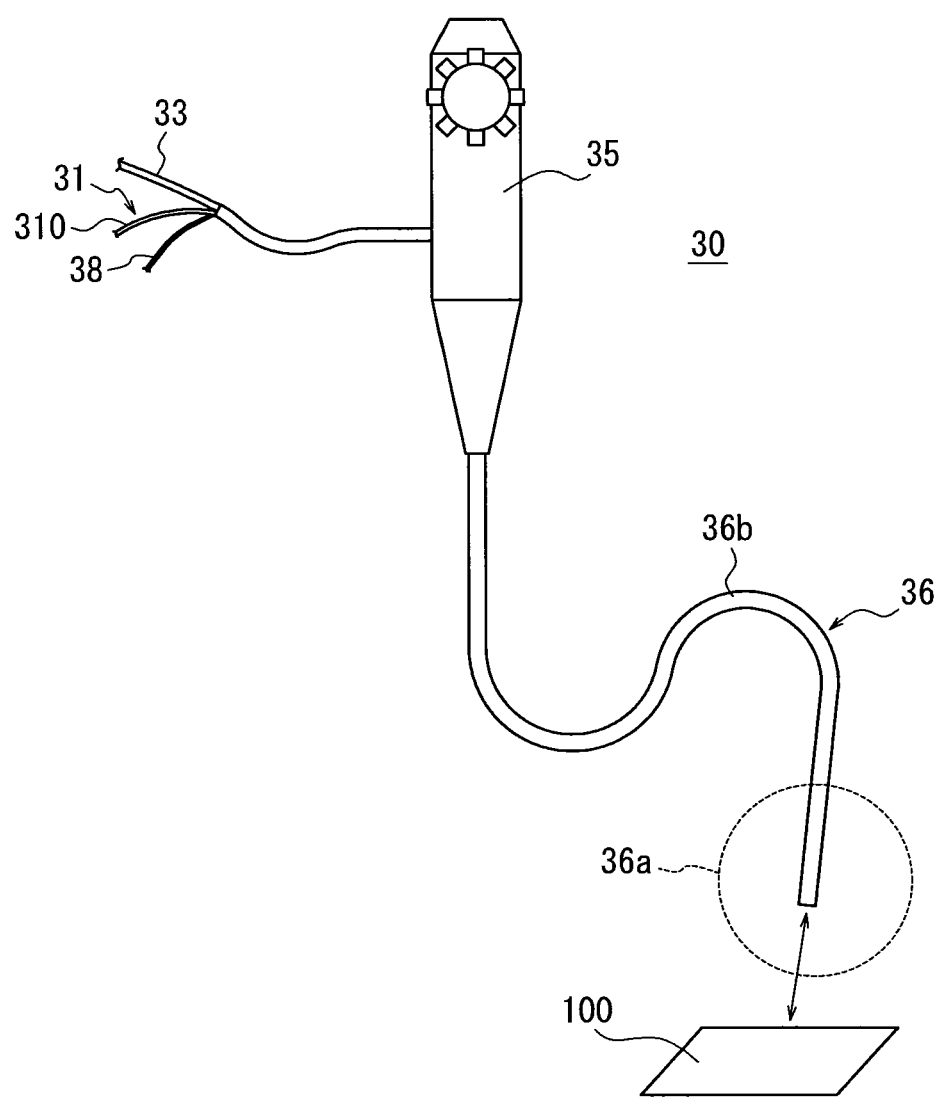
FIG. 2 is an overview schematically illustrating the scope of FIG. 1.

FIG. 2 is an overview schematically illustrating the scope 30. The scope 30 includes an operation portion 35 and an insertion portion 36. The illumination optical fiber 31 and the detection fiber bundle 33 are installed as being extended from the operation portion 35 up to the tip part 36a (indicated by the broken line of FIG. 2) of the insertion portion 36, and detachably connected respectively to the control apparatus body 50. Further, the scope 30 includes a wiring cable 38 connected to the optical scanning actuator 40 and extending from the insertion portion 36 through the operation portion 35. The wiring cable 38 is detachably connected to the drive controller 54 via a connection connector 39, as illustrated in FIG. 1. Here, the insertion portion 36 is configured as a flexible part 36b that is capable of bending, except for the tip part 36a configured as a hard part that do not bend.

Figure 3:
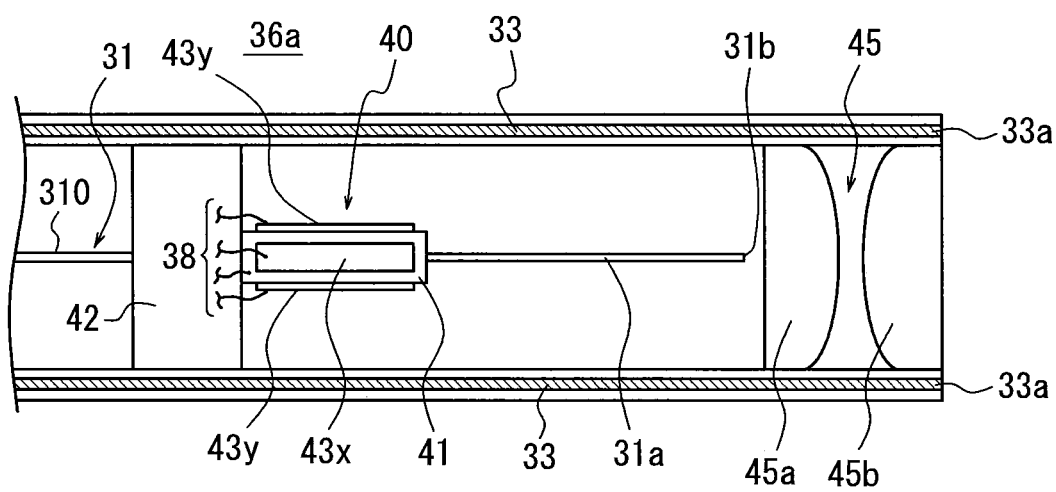
FIG. 3 is an enlarged sectional view of the tip part of the scope of FIG. 2.

FIG. 3 is art enlarged sectional view of the tip part 36a of the scope 30 of FIG. 2. The optical scanning actuator 40 and an illumination optical system 45 are installed in the tip part 36a. FIG. 3 illustrates a case where the illumination optical system 45 is formed of two projection lenses 45a, 45b. The optical scanning actuator 40 includes a ferrule 41 that supports an emission end 31a of the illumination optical fiber 31 passing therethrough. The illumination optical fiber 31 is fixedly adhered to the ferrule 41. The ferrule 41 is joined to a support 42 at an end opposite to the emission end face 31b of the illumination optical fiber 31 so as to be oscillatably cantilevered by the support 42. The illumination optical fiber 31 extends as penetrating through the support 42.

The ferrule 41 is formed of metal such as nickel. The ferrule 41 may be formed in an arbitrary outer shape, such as a rectangular column shape or a cylinder shape. The ferrule 41 has piezoelectric elements 43x and 43y mounted thereon, the piezoelectric elements 43x and 43y opposing to each other in the x-direction and in the y-direction, respectively, the x-direction and the y-direction being mutually orthogonal to each other in a plane perpendicular to the z-direction parallel to the optical axis direction of the illumination optical fiber 31. FIG. 3 shows only one piezoelectric element 43x. The piezoelectric elements 43x and 43y are each in a rectangular shape elongated in the z-direction. The piezoelectric elements 43x and 43y each have electrodes formed on both faces in the thickness direction, and are configured to extend and contract in the z-direction when applied with a voltage in the thickness direction via the opposing electrodes.

The piezoelectric elements 43x and 43y are each adhered to the ferrule 41 via one electrode surface while having the other electrode surface connected to the corresponding wiring cable 38. Similarly, the ferrule 41 serving as a common electrode of the piezoelectric elements 43x and 43y is connected to the corresponding wiring cable 38. The two opposing piezoelectric elements 43x in the x-direction are applied with an alternating voltage of the same phase from the drive controller 54 of FIG. 1 via the corresponding wiring cable 38. Similarly, the two opposing piezoelectric elements 43y in the y-direction are applied with an alternating voltage of the same phase from the drive controller 54 via the corresponding wiring cable 38.

In this manner, one of the two piezoelectric elements 43x extends while the other contracts, to generate bending vibration in the x-direction in the ferrule 41. Similarly, one of the two piezoelectric elements 43y extends while the other contracts, to generate bending vibration in the y-direction in the ferrule 41. As a result, the x-direction vibration and the y-direction vibration of the ferrule 41 are combined, so that the ferrule 41 is deflected integrally with the emission end 31a of the illumination optical fiber 31. Accordingly, when illumination light is caused to incident on the illumination optical fiber 31, the observation object can be two-dimensionally scanned with the illumination light emitted from the emission end face 31b.

The detection fiber bundle 33 passes through the outer periphery of the insertion portion 36 to extend up to the tip of the tip part 36a. A detection lens, though not illustrated, may be disposed at the tip part 33a of each fiber of the detection fiber bundle 33.

The projection lenses 45a, 45b are disposed in the extreme tip of the tip part 36a. The projection lenses 45a, 45b are configured to converge, onto a predetermined focal position, laser light emitted from the emission end face 31b of the illumination optical fiber 31. When the detection lens is disposed at the tip part 33a of the detection fiber bundle 33, the detection lens is arranged so as to take in, as signal light, light resulting from laser light irradiated onto the object 100 and reflected, scattered, and refracted by the object 100 (light that has been interacted with the object 100) or fluorescence, so as to have the light converged and coupled to the detection fiber bundle 33. The illumination optical system 45 may be formed of one lens or three or more lenses, without being limited to the two projection lenses 45a, 45b.

Figure 4:
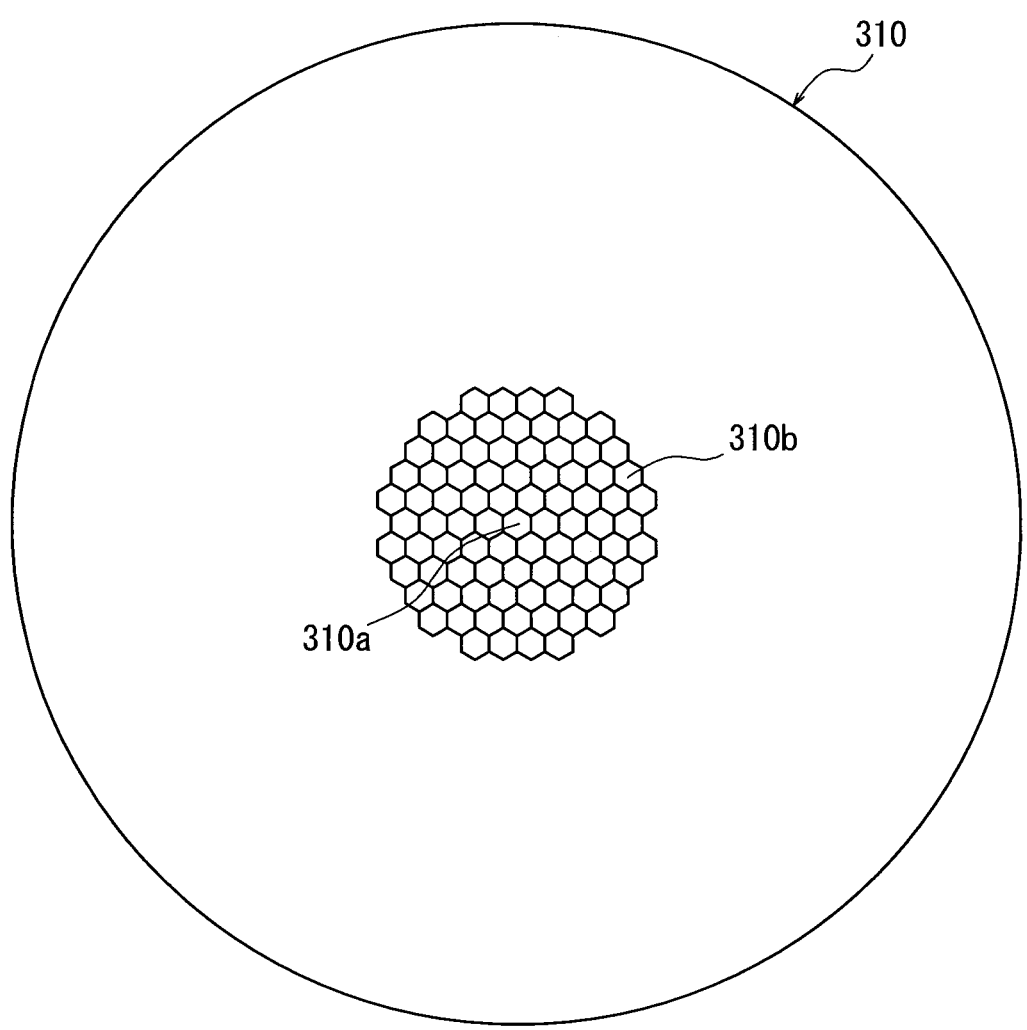
FIG. 4 is a sectional view of the photonic crystal fiber.

In the aforementioned configuration, the illumination optical fiber 31 and the optical scanning actuator 40 installed in the scope 30 form an optical fiber scanner. In Embodiment 1, the illumination optical fiber 31 is formed, in its entirety, of a photonic crystal fiber 310. The photonic crystal fiber 310 is configured by having voids 310b regularly formed around a core 310a through which laser light propagates, as illustrated in section of FIG. 4. The photonic crystal fiber 310 operates in single mode in a wavelength band used, and has a feature in that it can undergo strong bending without suffering hardly any bending loss.

According to the scanning endoscope apparatus 10 of Embodiment 1, the illumination optical fiber 31 installed in the scope 30 is formed of the photonic crystal fiber 310, which means that the insertion portion 36 of the scope 30 suffers hardly any loss of illumination light even when inserted, for example, into a body cavity and applied with a strong bending (of, for example, a curvature radius of 10 mm or less and the bending angle of 110° or larger) within the body cavity, without causing any change in color balance or reduction in absolute brightness of the illumination light, to thereby generate an image of excellent image quality. Here, in the photonic crystal fiber 310, the voids 310b may preferably be sealed at the emission end face in order to prevent intrusion of dust, moisture, and the like, into the voids 310b. In this manner, the illumination light spatially output from the core 310a can be prevented from suffering chronological change in beam diameter, with the result that the beam spot diameter of illumination light on the object 100, which otherwise affects resolution, can be prevented from being changed.

Embodiment 2

Figure 5:
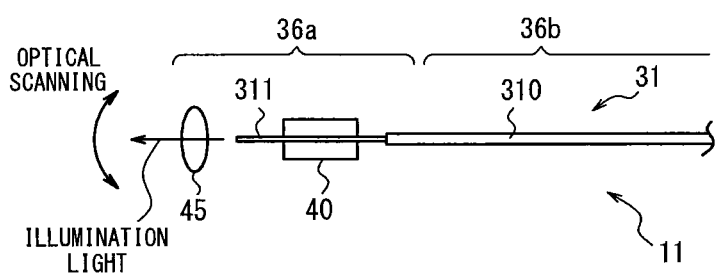
FIG. 5 is a view for illustrating the disclosed scanning endoscope apparatus according to Embodiment 2.

FIG. 5 is a view for illustrating the disclosed scanning endoscope apparatus according to Embodiment 2. The scanning endoscope apparatus 11 of Embodiment 2 is similar to the scanning endoscope apparatus 10 of Embodiment 1 except in that the illumination optical fiber 31 forming the optical fiber scanner is formed of the photonic crystal fiber 310 and a single mode fiber 311 fused to the emission end face thereof. The entire single mode fiber 311, including a part fused with the photonic crystal fiber 310, is positioned inside the tip part 36a formed of a hard part of the scope 30, and the emission end 311a of the single mode fiber 311 is displaced by the optical scanning actuator 40. The rest of the configuration is similar to that of Embodiment 1, and thus the description thereof is omitted.

According to the scanning endoscope apparatus 11 of Embodiment 2, the single mode fiber 311 is fused to the emission end face of the photonic crystal fiber 310, to thereby seal the voids 310b at the emission end face of the photonic crystal fiber 310. When directly sealing the voids 310b at the emission end face of the photonic crystal fiber 310, the beam diameter of light spatially output therefrom may vary depending on the sealing state (such as sealing rate and sealing length), making it difficult to control quality. The disclosed scanning endoscope apparatus 11 is capable of stabilizing the beam diameter spatially output from the emission end face 311b of the single mode fiber 311, and thus can stably generate an image with excellent image quality. Further, the photonic crystal fiber 310 and the single mode fiber 311 are fused to each other at a position within the tip part 36a formed of a hart part of the scope 30, which allows for stably maintaining the fused state without being affected by the bending of the insertion portion 36. In Embodiment 2, the single mode fiber 311 may preferably be smaller in outer diameter. For example, when the photonic crystal fiber 310 has an outer diameter of 125 μm, the single mode fiber 311 with an outer diameter of, for example, 80 μm may be used, which is smaller than 125 μm. This configuration reduces the mass of the single mode fiber 311, allowing the optical scanning actuator 40 to more largely vibrate the single mode fiber 311, to thereby optically scan the object 100 across a wider range.

Embodiment 3

Figure 6:
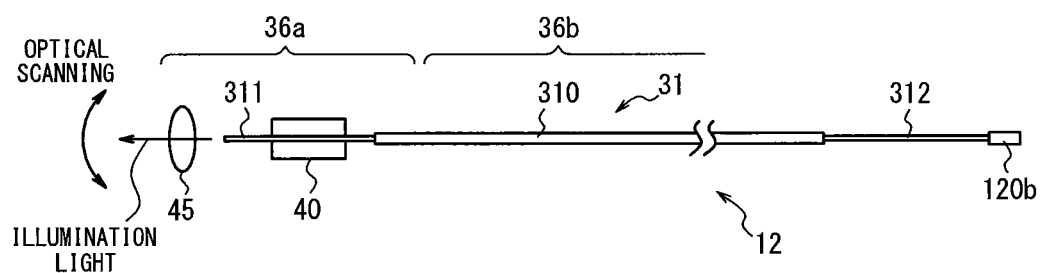
FIG. 6 is a view for illustrating the disclosed scanning endoscope apparatus according to Embodiment 3.

FIG. 6 is a view for illustrating the disclosed scanning endoscope apparatus of Embodiment 3. The scanning endoscope apparatus 12 of Embodiment 3 is different from the scanning endoscope apparatus 11 of Embodiment 2, in that the illumination optical fiber 31 forming an optical fiber scanner further includes a single mode fiber 312 fused to the incident end face of the photonic crystal fiber 310. The single mode fiber 312 is disposed at a position between the light source section 53 and the operation portion 35 so that the photonic crystal fiber 310 is disposed in the flexible part 36b of the scope 30. The single mode fiber 312, with an optical connector 120b joined at the incident end thereof, is detachably joined to an optical connector 120a of the light source section 53 via the adapter 110. The rest of the configuration is similar to that of Embodiment 2, and thus the description thereof is omitted.

According to the scanning endoscope apparatus 12 of Embodiment 3, the single mode fiber 312 is fused to the incident end face of the photonic crystal fiber 310, to thereby seal the voids 310b at the incident end face of the photonic crystal fiber 310. Therefore, the beam diameter spatially output from the illumination optical fiber 31 can be stabilized, which allows for generating an image with excellent image quality. In Embodiment 3, the single mode fiber 312 and the second fiber 58 of the light source section 53 may desirably be configured as the same single mode fiber.

Embodiment 4

Figure 7:
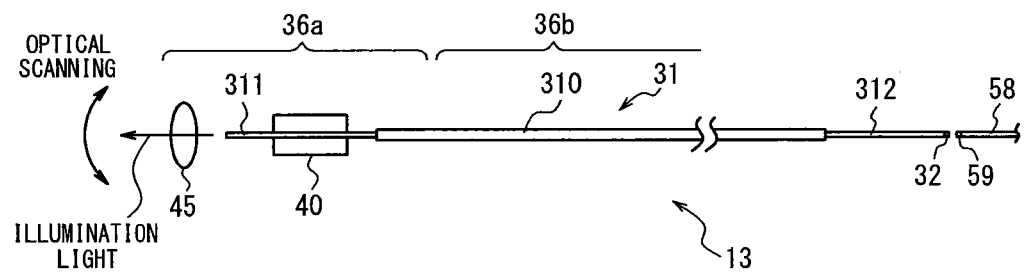
FIG. 7 is a view for illustrating the disclosed scanning endoscope apparatus according to Embodiment 4.

FIG. 7 is a view for illustrating the disclosed scanning endoscope apparatus according to Embodiment 4. The scanning endoscope apparatus 13 of Embodiment 4 includes, in the scanning endoscope apparatus 12 of Embodiment 3, a gradient index lens (GRIN lens) 59 fused to the emission end face of the second fiber 58 of the light source section 53 and a GRIN lens 32 fused to the incident end face of the single mode fiber 312 of the optical fiber scanner.

Figure 8:
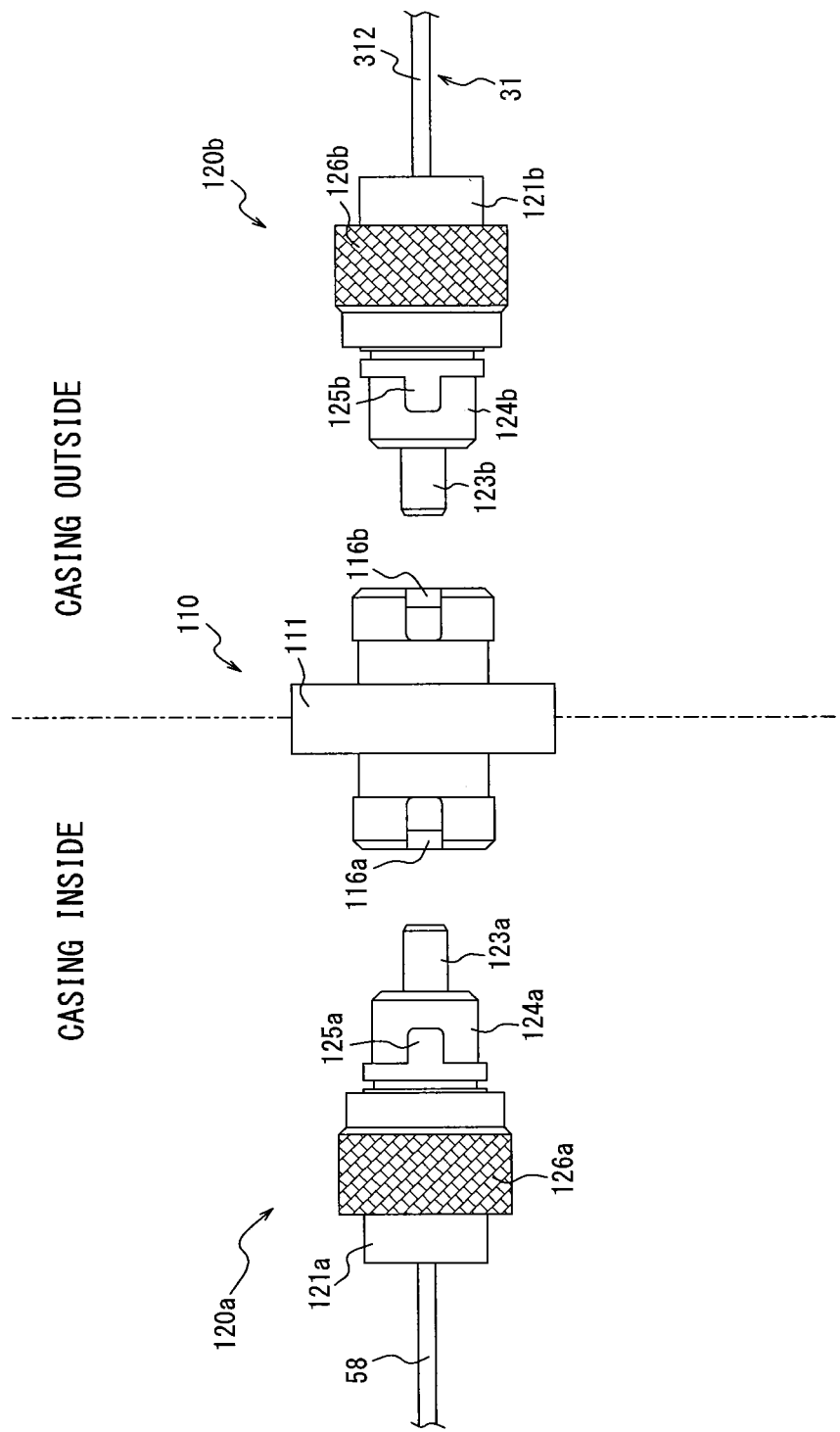
FIG. 8 is an external view illustrating configurations of the disclosed optical connector and adapter not joined to each other, according to Embodiment 4.
Figure 9:
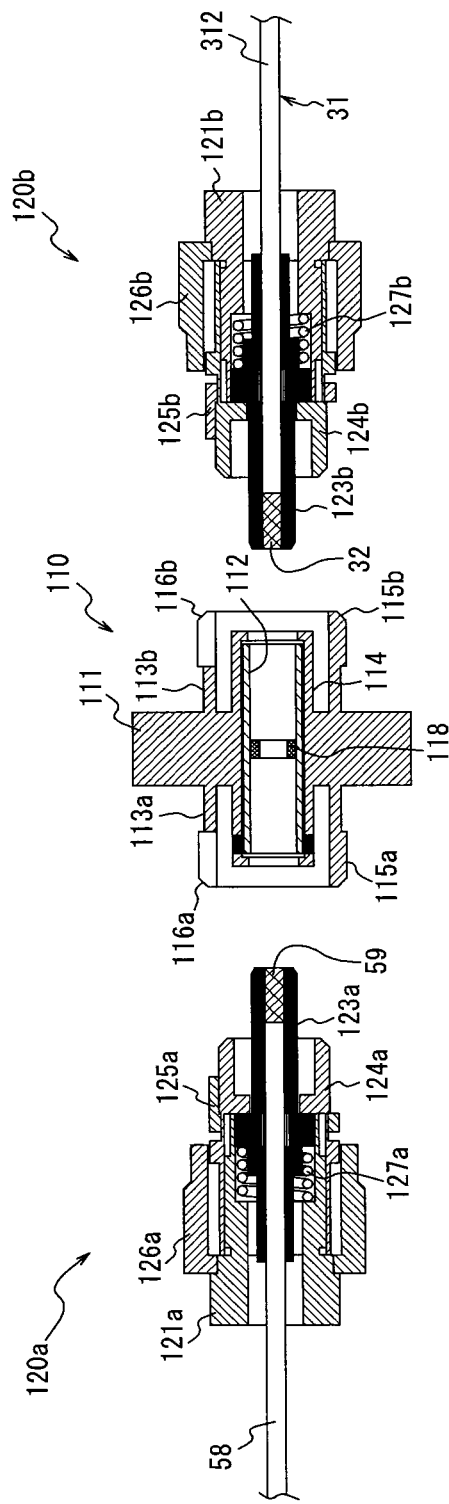
FIG. 9 is a sectional view of the optical connector and the adapter of FIG. 8 not joined to each other.
Figure 10:
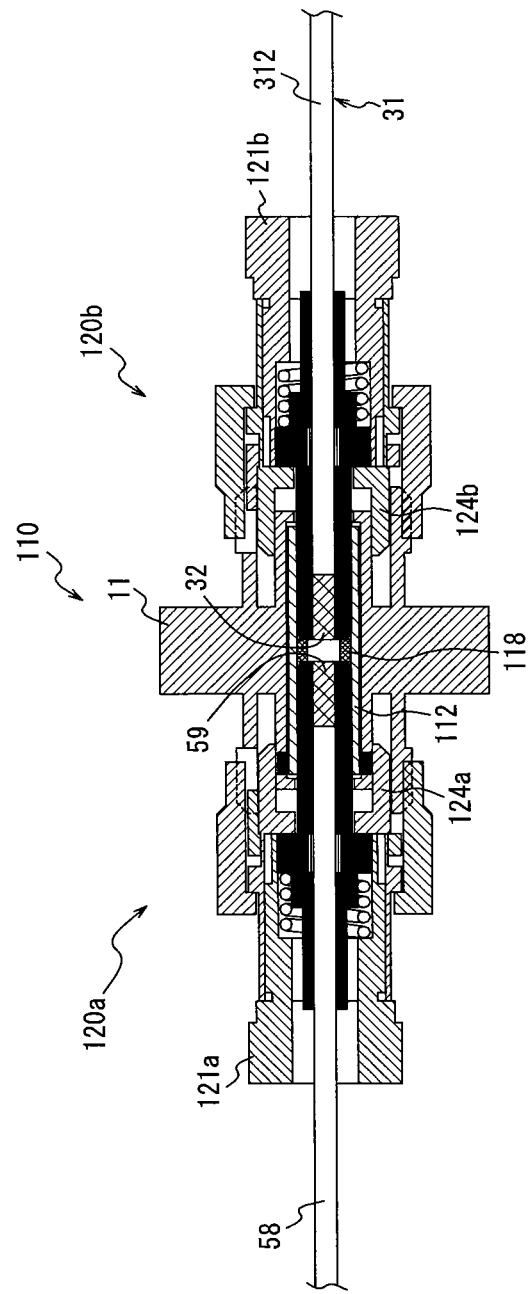
FIG. 10 is a sectional view of the optical connector and the adapter of FIG. 8 joined to each other.

FIGS. 8, 9, and 10 illustrate configurations of the optical connector 120a, the adapter 110, and the optical connector 120b each detachably joining the second fiber 58 of the light source section 53 to the single mode fiber 312 of the optical fiber scanner. FIGS. 8 and 9 each are an external view and a sectional view, respectively, illustrating the optical connectors 120a and 110b not joined to each other, and FIG. 10 is a sectional view illustrating the optical connectors 120a and 110b joined to each other.

The adapter 110 is fixed to the casing of the control apparatus body 50 or of the light source section 53, so as to detachably join the optical connector 120a joined to the second fiber 58 with the optical connector 120b joined to the single mode fiber 312 of the optical fiber scanner, between the casing inside and the casing outside. The adapter 110 includes an adapter housing 111 and a split sleeve 112. The adapter housing 111 includes an outer cylinder 113a having an opening on the casing inside, and an outer cylinder 113b having an opening on the casing outside. The outer cylinders 113a, 113b have, on the inside thereof, an inner cylinder 114 having a cavity between the optical connector 120a side and the optical connector 120b side. A cylindrical split sleeve 112 is disposed inside the cavity of the inner cylinder 114. The inner cylinder 114 has an inner periphery protruding inward at both ends so as to prevent the split sleeve 112 from being detached. The outer cylinders 113a, 113b have outer screws 115a, 115b formed on the outer circumferential end sides. Groove-shaped key receivers 116a, 116b are formed in part of the inner peripheries of the outer cylinders 113a, 113b. As described above, two connector connection parts opposing to each other are formed on the casing inside and the casing outside of the adapter housing 111, each having a shape capable of connecting the optical connector 120a and the optical connector 120b to each other.

The split sleeve 112 is a hollow tubular member having a slit extending in the longitudinal direction (direction along the center axis when disposed inside the inner cylinder 114), and formed of hard ceramics such as zirconium. A dustproof ring 117 (shielding member) is arranged between the inner cylinder 114 and the split sleeve 112 on the optical connector 120a side of the casing inside and along the outer circumference of the split sleeve 112. The dustproof ring 117, which is made of, for example, a high-elastic rubber, serves to shield the casing inside and the inner cylinder 114 inside the adapter housing 111. The dustproof ring 117 is designed to be light-shielded by the adapter housing 111 and casings so as not to receive external ultraviolet light. This configuration prevents degradation of the dustproof ring 117.

The adapter 110 has a PD built-in spacer 118 including a photodetector (PD), within the split sleeve 112 and at an intermediate between the optical connector 120a side and the optical connector 120b side. Signals from the photodetector (PD) can be monitored from outside of the adapter 110.

The optical connector 120a is configured by including a connector housing 121a, and a ferrule 123a incorporating the tip part of the second fiber 58. Hereinafter, the tip direction of the second fiber 58 of the optical connector 120a is referred to as forward, and the direction opposite thereto is referred to as backward.

The connector housing 121a has a tip portion formed as a cylinder 124a having a cylindrical wall, which is shaped to fit into a gap between the inner cylinder 114 and the outer cylinder 113a of the adapter 110. A key 125a is protrudingly formed on the outer periphery of the cylinder 124a. The key 125a is fit into the key receiver 116a of the adapter 110 when coupling the adapter 110 to the optical connector 120a, so as to perform accurate positioning of the adapter 110 and the optical connector 120a in the rotation direction.

A coupling nut 126a is formed on the outer periphery of the connector housing 121a, as being rotatable and movable in the fiber optical axis direction within a specific range. The coupling nut 126a has an inner screw formed on the inner surface, which is configured to mesh with an outer screw 115a of the outer cylinder 113a of the adapter housing 111.

The ferrule 123a is in a cylindrical column shape with a chamfered tip, and has, along the center axis thereof, the emission end of the second fiber 58 inserted therethrough. The GRIN lens 59 is fused to the emission end face of the second fiber 58. The cylindrical column part of the ferrule 123a protrudes forward from the center of the cylinder 124a of the connector housing 121a and supported via the periphery by the connector housing 121a at the back of the cylinder 124a. A flange is formed on the backward of the ferrule 123a, allowing the ferrule 123a to slide against the inner periphery of the adapter housing 111 in the optical axis direction of the second fiber 58 within the adapter housing 111, while being biased forward by a spring 127a disposed inside the adapter housing 111.

The optical connector 120b is similarly configured as the optical connector 120a, and thus the same components are denoted by the same reference numerals with the suffix b, to omit the description thereof. The optical connector 120a basically remains in the connected state for a lengthy period, while the optical connector 120b is detached and attached more frequently than is the optical connector 120a.

When connecting the optical connectors 120a, 120b to the adapter 110, the tip part of the adapter 110 and the tip parts of the optical connectors 120a, 120b are first aligned such that the both axes coincide with each other, and positioned in the rotation direction such that the keys 125a, 125b of the optical connectors 120a, 120b are fit into the key receivers 116a, 116b of the adapter 110. Then, the ferrules 123a, 123b are fit into the split sleeve 112, and the cylinders 124a, 124b of the optical connectors 120a, 120b are fit in between the outer cylinders 113a, 113b and both ends of the inner cylinder 114 of the adapter 110.

Next, the coupling nuts 126a, 126b are moved to the adapter 110 side and rotated. As a result, the outer screw 115a of the adapter housing 111 and the inner screw of the coupling nut 126a mesh with each other, so as to advance the coupling nuts 126a, 126b toward the adapter 110 side. Along therewith, the ferrule 123a further slides forward within the split sleeve 112.

When the tip ends of the ferrules 123a, 123b abut to the PD spacer 118, the ferrules 123a, 123b and the PD built-in spacer 118 are pressed against each other by means of the springs 127a, 127b in the optical connectors 120a, 120b with a spring force equal to or smaller than a certain level not to damage the tip ends of the ferrules 123a, 123b. The rotations of the coupling nuts 126a, 126b are regulated by steps 128a, 128b formed on the outer peripheries of the connector housings 121a, 121b, so as not to generate any excessive pressing force on the ferrules 123a, 123b against the PD spacer 118.

According to the scanning endoscope apparatus 13 of Embodiment 4, when the optical connectors 120a and 120b are connected to the adapter 110, the ferrule 123a and the ferrule 123b are fixed within the split sleeve 112 across the PD built-in spacer 118 interposed therebetween, as illustrated in FIG. 10. In this manner, the GRIN lens 59 fused to the emission end face of the second fiber 58 and the GRIN lens 32 fused to the incident end face of the single mode fiber 312 of the optical fiber scanner coaxially face each other via a gap therebetween. Accordingly, the second fiber 58 and the single mode fiber 312 can be joined to each other with high connection efficiency, to thereby obtain the same effect as that of Embodiment 3.

Further, in Embodiment 4, the second fiber 58 and the single mode fiber 312 are not brought into physical contact with each other, which can reduce the risk of breaking the fiber tip when connecting the optical connectors 120a, 120b. Accordingly, the optical connectors 120a, 120b may repeatedly be connected while maintaining high connection efficiency, without the need for any special operation (such as end face cleaning) for maintaining connection efficiency. Further, when part of light emitted from the second fiber 58 fails to incident on the core of the single mode fiber 312, the part of light is incident on the photodetector of the PD built-in spacer 118. Therefore, the output of the photodetector can be monitored to monitor the connection efficiency between the optical connectors 120a, 120b.

In Embodiment 4, the GRIN lens 59 of the light source section 53, the second fiber 58 fused with the GRIN lens 59, the GRIN lens 32 of the optical fiber scanner, and the single mode fiber 312 fused with the GRIN lens 32 may desirably be equal to one another in outer diameter. This configuration allows the second fiber 58 and the GRIN lens 59 to be accurately mounted to the ferrule 123a of the optical connector 120a, and the single mode fiber 312 and the GRIN lens 32 to be accurately mounted to the ferrule 123b of the optical connector 120b, which facilitates optical adjustment of the ferrules 123a, 123b, to thereby readily obtain high connection efficiency.

The present disclosure is not limited to Embodiments above, and may be subjected to a number of modifications and alterations. For example, in Embodiments 1 to 3, the optical connectors 120a, 120b may be configured similarly to the optical connectors 120a, 120b of FIGS. 8, 10, and the adapter 110 may be configured without the PD built-in spacer 118 of FIGS. 9 and 10. In this case, when the tip end of the ferrule 123a of the optical connector 120a and the tip end of the ferrule 123b of the optical connector 120b abut to each other inside the adapter 110, the emission end face of the second fiber 58 and the incident end face of the illumination optical fiber 31 are pressed against each other with a spring force equal to or smaller than a certain level not to cause any damage thereto, by means of the springs 127a, 127b in the optical connectors 120a.

The illumination optical fiber 31 of the optical fiber scanner may have the incident end face thereof directly fused to the emission end face of the second fiber 58 of the light source section 53. In this case, as in Embodiment 3, when the illumination optical fiber 31 fused to the second fiber 58 is formed of the single mode fiber 312, the single mode fiber 312 and the second fiber 58 may desirably be formed of the same single mode fiber. With this configuration, high connection efficiency can be obtained. Further, in Embodiment 1, the single mode fiber 312 may be fused to the incident end of the photonic crystal fiber 310 as in Embodiment 3, so as to be joined to the light source section 53 via the single mode fiber 312. Further, in Embodiment 1, the emission end face of the second fiber 58 and the incident end face of the photonic crystal fiber 310 may each be fused with a GRIN lens, and joined to each other as in Embodiment 4.

The optical scanning actuator 40 may employ, without being limited to the piezoelectric system, other publicly known drive method such as electromagnetic systems using coils and permanent magnets. Further, the detection fiber is not limited to a multimode fiber or bundle. In Embodiments above, the first fibers 56R, 56G, 56B may be omitted, and the light source section 53 may be configured to spatially multiplex, by the coupler 57, lasers spatially output from the lasers 55R, 55G, 55B and have the resulting laser incident on the second fiber 58. Further, the present disclosure is applicable to a scanning microscope or a scanning projector apparatus, without being limited to the scanning endoscope apparatus.

REFERENCE SIGNS LIST

10, 11, 12, 13 scanning endoscope apparatus
30 scope (endoscope)
31 illumination optical fiber
32 gradient index lens (GRIN lens)
33 detection fiber bundle
36*a* tip part (hard part)
40 optical scanning actuator
50 control apparatus body (casing)
53 light source section
55R, 55G, 55B laser
56R, 56G, 56B first fiber
57 coupler
58 second fiber
59 gradient index lens (GRIN lens)
110 adapter
120*a*, 120*b* optical connector
310 photonic crystal fiber
311, 312 single mode fiber

The invention claimed is:

1. A scanning endoscope apparatus, comprising:
a casing having a light source section; and
an optical fiber scanner comprising:
an optical scanning actuator to displace an emission end of an optical fiber and scanning light emitted from the optical fiber, the optical fiber includes a photonic crystal fiber at least in a propagation path of the light leading to the optical scanning actuator; the optical fiber includes a single mode fiber fused to an emission end face of the photonic crystal fiber, the single mode fiber being displaced, at the emission end thereof, by the optical scanning actuator
wherein:
the light source section comprises: a plurality of lasers that emit laser lights of different wavelengths; a coupler that multiplexes laser lights from the plurality of lasers; and a fiber that propagates light emitted from the coupler; and
the optical fiber scanner is disposed in a scope detachably connected to the casing such that the entire single mode fiber including a part where the single mode fiber is fused to an emission end face of the photonic crystal fiber is positioned inside a hard part of the tip part of the scope, the optical scanning actuator displaces an emission end of the single mode fiber, and an incident end face of the optical fiber is optically coupled to the emission end face of the fiber propagating light emitted from the coupler when the scope is connected to the casing.

2. The optical fiber scanner according to claim 1, wherein the single mode fiber fused to the emission end face of the photonic crystal fiber is smaller in outer diameter than the photonic crystal fiber.

* * * * *